United States Patent
Koshimura et al.

(10) Patent No.: US 10,858,640 B2
(45) Date of Patent: Dec. 8, 2020

(54) PRODUCTION FOR RECOMBINANT HUMAN DNASE I

(71) Applicant: JCR PHARMACEUTICALS CO., LTD., Ashiya (JP)

(72) Inventors: Yuri Koshimura, Kobe (JP); Miroslav Matev, Kobe (JP); Hiroyuki Sonoda, Kobe (JP)

(73) Assignee: JCR PHARMACEUTICALS CO., LTD., Ashiya (JP)

( * ) Notice: Subject to any disclaimer, the term of this patent is extended or adjusted under 35 U.S.C. 154(b) by 0 days.

(21) Appl. No.: 15/581,927

(22) Filed: Apr. 28, 2017

(65) Prior Publication Data

US 2017/0233704 A1    Aug. 17, 2017

Related U.S. Application Data

(63) Continuation of application No. PCT/JP2015/079408, filed on Oct. 19, 2015.

(30) Foreign Application Priority Data

Oct. 31, 2014 (JP) ................. 2014-235042

(51) Int. Cl.
*C12N 9/22* (2006.01)
*C12N 9/16* (2006.01)
*C12N 15/09* (2006.01)

(52) U.S. Cl.
CPC ............... *C12N 9/22* (2013.01); *C12N 9/16* (2013.01); *C12Y 301/21001* (2013.01); *C12N 15/09* (2013.01)

(58) Field of Classification Search
None
See application file for complete search history.

(56) References Cited

U.S. PATENT DOCUMENTS

| | | | |
|---|---|---|---|
| 7,297,526 B2 * | 11/2007 | Shak | ........... C12N 9/22 435/196 |
| 2003/0044403 A1 | 3/2003 | Shak | |
| 2003/0054532 A1 | 3/2003 | Chan et al. | |
| 2003/0229212 A1 | 12/2003 | Fahrner et al. | |
| 2013/0244231 A1 | 9/2013 | Takahashi | |
| 2013/0330802 A1 | 12/2013 | Mihara et al. | |

FOREIGN PATENT DOCUMENTS

| | | |
|---|---|---|
| WO | WO 90/07572 A1 | 7/1990 |
| WO | WO 93/25670 A1 | 12/1993 |
| WO | WO 95/23854 A1 | 9/1995 |
| WO | WO 2012/063799 * | 5/2012 |
| WO | WO 2012/063799 A1 | 5/2012 |
| WO | WO 2014/016873 A1 | 1/2014 |

OTHER PUBLICATIONS

Paidel, H.K., Thesis, Structures of Deoxyribonuclease I from mammalian Sources Oklahoma State University May 1985.*
Rosennond-Hornbeak et al. (Journal of Biological Chemistry, vol. 249, No. 10, pp. 3287-3291, 1974.*
Methods of Analysis of Food Components and additives,Ed. Otles, Pub. CRC Press, Baton Rouge FL, pp. 83-84, 2005.*
Wadano et al., Biochemistry vol. 18, pp. 4124-4130, 1979.*
Haruo Takeshita, et al., "Use of Human Recombinant DNase I Expressed in COS-7 Cells as an Immunogen to Produce a Specific Anti-DNase I Antibody" Experimental and Clinical Immunogenetics, vol. 18, XP9158770, 2001, pp. 226-232.
International Search Report dated Jan. 19, 2016 in PCT/JP2015/079408.
Steven Shak, et al., "Recombinant human DNase I reduces the viscosity of cystic fibrosis sputum", Proc. Natl. Acad. Sci., Medical Science, vol. 87, Dec. 1990, pp. 9188-9192.
Joanne M. Quan, et al., "A two-year randomized, placebo-controlled trial of dornase alfa in young patients with cystic fibrosis with mild lung function abnormalities", The Journal of Pediatrics, vol. 139, No. 6, 2001, pp. 813-820.
Kazuo Ito, et al., "Human Urine DNase I: Immunological Identity with Human Pancreatic DNase I, and Enzymic and Proteochemical Properties of the Enzyme", J. Biochem. 95. 1984, pp. 1399-1406.

* cited by examiner

*Primary Examiner* — Richard G Hutson
(74) *Attorney, Agent, or Firm* — Oblon, McClelland, Maier & Neustadt, L.L.P.

(57) ABSTRACT

Disclosed is a method for production of recombinant human DNase I which is of such high purity as may be directly used as a medical drug. The method includes the steps of; culturing recombinant DNase I-producing mammalian cells, subjecting a culture supernatant to an anion-exchange column chromatography, subjecting to a column chromatography employing as solid phase a material having affinity for phosphate group, subjecting to a cation-exchange column chromatography, and subjecting to a dye affinity column chromatography.

12 Claims, 5 Drawing Sheets

Specification includes a Sequence Listing.

PRODUCTION FOR RECOMBINANT HUMAN DNASE I

CROSS-REFERENCE TO RELATED APPLICATIONS

The present application is a continuation of and claims the benefit of priority to International Application No. PCT/JP2015/079408, filed Oct. 19, 2015, which is based upon and claims the benefit of priority to Japanese Patent Application No. 2014-235042, filed Oct. 31, 2014. The entire contents of these applications are incorporated herein by reference.

TECHNICAL FIELD

The present invention relates to a method for production of recombinant human DNase I, more specifically, to a method for purification of recombinant human DNase I, that secreted in culture medium by culturing mammalian cells producing recombinant human DNase I in a serum free medium, by using column chromatographies.

BACKGROUND ART

Cystic fibrosis is a genetic disease caused by malfunction of cAMP dependent $Cl^-$ channel (CFTR). CFTR has a function to generate an electrochemical gradient across a cell membrane by pumping out chloride iron from cells, suppress uptake of sodium ion into the cells, and elevate the osmotic pressure outside the cells. Increase of osmotic pressure outside the cells causes the efflux of water from the cells, and viscosity of mucosal fluid covering the cells kept low. When CFTR fails to function properly, the mucosal fluid is not supplied by water to increase its viscosity, which makes it difficult that the mucosal fluid moves, resulting the accumulation of viscous secretion in bronchi and the like. If the accumulated viscous secretion is infected with bacteria such as *Pseudomonas aeruginosa*, a large number of neutrophils or the like are mobilized, and as the results, DNA is released from the dead cells of neutrophils and the viscosity of mucosal fluid further increases.

Primary clinical events of this disease include digestion and absorption disorders caused by hyposecretion of pancreatic enzyme and chronic obstructive pulmonary disease symptoms caused by viscous secretion in bronchus. Incidence of this disease is reported to be about one case in every 2,500 live birth in western countries, but to be very rare in East Asian countries including Japan. Many of the patients die before or in their 30s by chronic repetitive respiratory tract infection caused by mucoid-type *Pseudomonas aeruginosa*.

Human DNase I (hDNase I) is a glycoprotein, having molecular weight of about 37 kD and consisting of 260 amino acid residues. This enzyme has an endonuclease activity and non-specifically degrades DNA to produce dinucleotide, trinucleotide, and oligonucleotide which possess 5'-phosphate group and 3'-hydoxyl group ends. The main physiological role of hDNase I is to digest DNA contained in food in digestive organs.

The gene encoding hDNase I was isolated in 1990, and recombinant DNase I (rhDNase I) has been produced as a glycoprotein having molecular weight of about 35 kD (patent document 1, non patent document 1).

DNase I has an activity to hydrolyze DNA contained in the viscous secretion in respiratory tract and reduce its viscosity (non patent document 1). By focusing on the activity of DNase I, therapies for cystic fibrosis using DNase I have been conducted from the 1950s onward, aiming to reduce the viscosity of the viscous secretion in the respiratory tract of patients with cystic fibrosis and facilitate removal of the viscous secretion from the respiratory tract, showing that DNase I exerts beneficial effect such as the improvement of lung function of patients with cystic fibrosis. Though initially DNAaseI derived from bovine pancreas had been used, as reported were severe adverse events including allergy reactions which seemed to be caused by contaminants, currently rhDNase I has been used. The medicament of cystic fibrosis containing this rhDNase I as an active ingredient is commercially available under the name of PULMOZYME (registered trademark).

When administered to the affected area, the drug solution containing PULMOZYME is nebulized by a nebulizer, and the patient inhales the nebulized drug solution (non patent document 2). The administered PULMOZYME, mixed with the viscous secretion in respiratory tract, digests DNA in the viscous secretion and reduces its viscosity.

As for the method for production of rhDNase I, there is known a method to remove deamidated rhDNase I on a tentacle cation exchange chromatography or a heparin column chromatography in the course of purification (patent document 2). Further, a method for use of calcium iron at a concentration of 1 mM to 1 M to inhibit aggregation of rhDNase I in the course of purification is known (patent document 3). There is still known a method for use of a disaccharide to inhibit aggregation of rhDNase I in the course of its purification (patent document 4).

As described above, the methods for purification of rhDNase I have been reported. However if rhDNase I contains contaminants, its administration to patients may cause serious adverse events including allergenic reactions as reported when DNAaseI derived from bovine pancreas was administered. Therefore, the rhDNase I used as a medicinal drug shall be highly purified. Further, as rhDNase I is needed to be administered in large doses when used as a medicament for treating the patients suffering from cystic fibrosis, it should be produced efficiently and inexpensively. Therefore, development of methods for efficiently producing highly purified rhDNase I is sought.

PRIOR ART DOCUMENTS

Patent Documents

[Patent Document 1] WO1990/007572
[Patent Document 2] WO1993/025670
[Patent Document 3] WO1995/023854
[Patent Document 4] US2003/0054532

Non Patent Documemts

[Non Patent Document 1] Shak S. et al., Proc Natl Acad Sci. 87, 9188-92 (1990)
[Non Patent Document 2] Quan J M. et al., J Pediatr. 139, 813-(2001)

SUMMARY OF INVENTION

Technical Problem

Against the above background, the objective of the present invention is to provide a method for purifying rhDNase I efficiently from the culture of rhDNase I-producing cells to such a purity as allows its use as a medicament for cystic fibrosis.

Technical Solution

In a study for the above-mentioned object, the present inventors found that rhDNase I, which is contained in the culture supernatant of rhDNase I-producing cells cultured in a serum-free medium, can be efficiently purified to a high purity by the combination of an anion-exchange column chromatography, a column chromatography employing as solid phase a material having affinity for phosphate group, a cation-exchange column chromatography, and a dye ligand affinity column chromatography. The present invention was completed through further studies based on the finding.

Thus, the present invention provides what follows.

(1) A method for production of recombinant human DNase I comprising the steps of;

(a) culturing recombinant DNase I-producing mammalian cells in a serum-free medium to let them secrete the recombinant human DNase I in the medium, (b) collecting culture supernatant by removing the cells from the culture that is obtained in step (a) above, (c) subjecting the culture supernatant collected in step (b) above to an anion-exchange column chromatography to collect a fraction containing the recombinant human DNase I, (d) subjecting the fraction collected in step (c) above to a column chromatography employing as solid phase a material having affinity for phosphate group to collect a fraction containing the recombinant human DNase I, (e) subjecting the fraction collected in step (d) above to a cation-exchange column chromatography to collect a fraction containing the recombinant human DNase I, (f) subjecting the fraction collected in step (e) above to a dye affinity column chromatography to collect a fraction containing the recombinant human DNase I, in the order.

(2) The method for production according to (1) above, wherein the anion exchanger employed in the anion-exchange column chromatography is a strong anion exchanger.

(3) The method for production according to (2) above, wherein the strong anion exchanger has a trimethyl ammonium group.

(4) The method for production according to one of (1) to (3) above, wherein the material having affinity for phosphate group is fluoroapatite or hydroxyapatite.

(5) The method for production according to (4) above, wherein the material having affinity for phosphate group is hydroxyapatite.

(6) The method for production according to one of (1) to (5) above, wherein the cation exchanger employed in the cation-exchange column chromatography is a strong cation exchanger.

(7) The method for production according to (6) above, wherein the strong cation exchanger has a sulfo group.

(8) The method for production according to one of (1) to (7) above, wherein the dye employed in the dye affinity column chromatography is a triazine dye.

(9) The method for production of recombinant human DNase I, further comprising a step to subject the fraction containing the recombinant human DNase I obtained by the method for production according to one of (1) to (8) above to a gel filtration column chromatography to collect a fraction containing the recombinant human DNase I.

(10) The method for production according to one of (1) to (9) above, wherein the anion-exchange column chromatography is carried out in the presence of 0.5 to 2.0 mM calcium ions.

(11) The method for production according to one of (1) to (9) above, wherein the anion-exchange column chromatography is carried out in the presence of 0.8 to 1.2 mM calcium ions.

(12) The method for production according to one of (1) to (11) above, wherein the cation-exchange column chromatography is carried out in the presence of 2 to 20 mM calcium ions.

(13) The method for production according to one of (1) to (11) above, wherein the cation-exchange column chromatography is carried out in the presence of 8 to 12 mM calcium ions.

(14) The method for production according to one of (1) to (13) above, wherein the mammalian cells are introduced with an expression vector comprising a human elongation factor-1α promoter, a gene encoding rhDNase I downstream thereof, an internal ribosome entry site derived from 5' untranslated region of murine encephalomyelitis virus further downstream thereof, and a gene encoding a glutamine synthetase still further downstream thereof, and additionally a puromycin or neomycin resistance gene downstream of another gene expression regulatory site.

(15) The method for production according to (14) above, wherein the internal ribosome entry site is derived from 5' untranslated region of wild-type murine encephalomyelitis virus and part of two or more start codons in the internal ribosome entry site have been destroyed.

(16) The method for production according to (15) above, wherein the internal ribosome entry site comprises the nucleotide sequence set forth as SEQ ID NO:2.

(17) The method for production according to one of (1) to (13) above, wherein the mammalian cells is introduced with an expression vector comprising a human elongation factor-1α promoter, a gene encoding rhDNase I downstream thereof, an internal ribosome entry site derived from 5' untranslated region of murine encephalomyelitis virus further downstream thereof, and a gene encoding a glutamine synthetase still further downstream thereof, and additionally a dihydrofolate reductase gene downstream of another gene expression regulatory site.

(18) The method for production according to (17) above, wherein the internal ribosome entry site is derived from 5' untranslated region of wild-type murine encephalomyelitis virus and part of two or more start codons in the internal ribosome entry site have been destroyed.

(19) The method for production according to (18) above, wherein the internal ribosome entry site comprises the nucleotide sequence set forth as SEQ ID NO:2.

(20) The recombinant human DNase I produced by the method for production according to one of (1) to (19) above, having a specific activity of 960 U/mg or more.

(21) The recombinant human DNase I produced by the method for production according to one of (1) to (19) above, having a specific activity of 960 to 1000 U/mg.

Effect of Invention

The present invention enables to efficiently produce rhDNase I to such a purity as allows its use as a medicament for cystic fibrosis.

DESCRIPTION OF EMBODIMENTS

Figure 1:
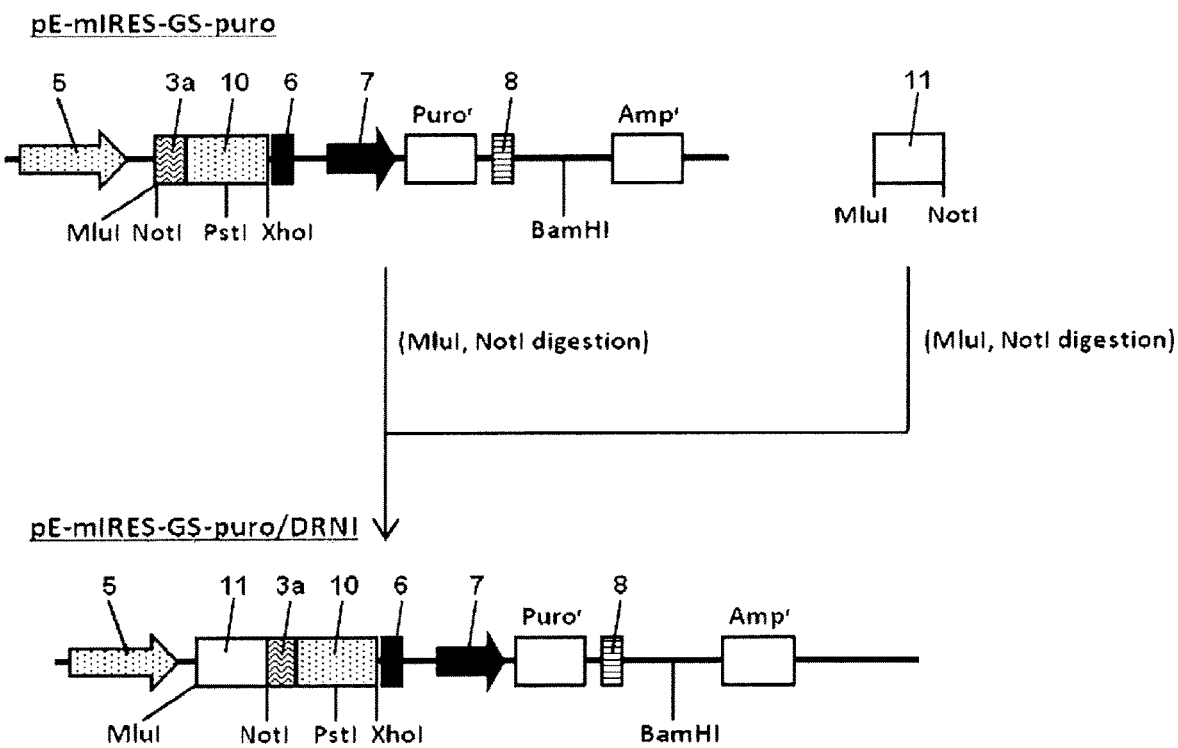
FIG. 1 illustrates the flow diagram of the method for construction of rhDNase I expression vector (pE-mIRES-GS-puro/DRN1).

The present invention relates to the method for production of recombinant human DNase I, in that method rhDNase I, contained in the culture supernatant of the culture medium of rhDNase I-producing cells cultured in a serum-free medium, is purified by the combination of an anion-exchange column chromatography, a column chromatography employing as solid phase a material having affinity for phosphate group, cation-exchange column chromatography, and a dye affinity column chromatography.

Naturally occurring human DNase I is a glycoprotein consisting of 260 amino acids. In the present invention, the term "human DNase I (hDNase I)" means in particular hDNase I having the same amino acid sequence as that of naturally occurring human DNase I, but not limited to this, includes any one of analogues of hDNase I which shows a DNase I activity, and in which one or more of amino acids constituting naturally occurring human DNase I are substituted, deleted or added. And the term "recombinant human DNase I (rhDNase I)" means the human DNase I (hDNase I) produced by using a genetic recombination technique.

In the present invention, rhDNase I is produced by culturing a mammalian cell, which is artificially manipulated so as to produce rhDNase I by expression or strong expression of a gene encoding hDNase I. In this end, the gene to be strongly expressed in the mammalian cells producing rhDNase I is generally introduced into the mammalian cell by transformation with an expression vector introduced with the gene, but not limited to this, it may be the intrinsic gene originally possessed by the mammalian cell but artificially modified so as to be strongly expressed. Examples of the means for artificially modifying an intrinsic gene to let it be strongly expressed include, but not limited to, replacing the promoter upstream of the intrinsic gene with a promoter which strongly induces expression of the gene. Further, though there is no particular limitation on the mammalian cells, cells derived from human, mouse, Chinese hamster are preferable, and CHO cells, the cells derived from Chinese hamster ovary cells, are particularly preferable. In the present invention, the term "rhDNase I" means particularly hDNase I secreted into the medium when mammalian cells producing rhDNase I are cultured.

There is no particular limitation as to the expression vector for incorporating and expressing the gene encoding hDNase I, provided that it has the potential to let the gene express when introduced into mammalian cells. The gene incorporated in the expression vector is placed downstream of a DNA sequence (gene expression regulatory site) capable of regulating the frequency of gene transcription in mammalian cells. The gene expression regulatory site that can be used in the present invention includes, for example, cytomegalovirus-derived promoter, SV40 early promoter, human elongation factor-1 alpha (EF-1 alpha) promoter, human ubiquitin C promoter and the like.

Mammalian cells, after introduction therein of such an expression vector, come to express the protein of interest that is incorporated into the expression vector. The levels of its expression, however, vary and are not even among those cells. Therefore, for an efficient production of the recombinant protein, a step is required to select, from the mammalian cells containing the expression vector introduced therein, those cells which express the protein of interest at high levels. For performing this selection step, a gene that acts as a selection marker is incorporated in an expression vector.

The most popular of such selection markers are enzymes (drug resistance markers) that decompose drugs such as puromycin, neomycin, and the like. Mammalian cells will be killed in the presence of these drugs beyond certain concentrations. Mammalian cells into which an expression vector has been introduced, however, become viable in the presence of those drugs because such cells can decompose the drugs with the drug selection markers incorporated in the expression vector and thus detoxify them or weaken their toxicity. When those cells, which have been introduced with an expression vector incorporated with a drug resistance marker, are successively cultured in a selective medium containing the drug corresponding to the drug resistance marker while gradually increasing the concentration of the drug, cells that can proliferate in the presence of the drug at relatively higher concentrations are obtained. Such cells that express a drug selection marker at high levels also tend to express, at high levels, a gene encoding a protein of interest incorporated together into the expression vector, and as a result, mammalian cells thus will be obtained that express the protein of interest at high levels.

As a selection marker, glutamine synthetase (GS) may also be used. Glutamine synthetase is an enzyme synthesized glutamine from glutamic acid and ammonia. Mammalian cells die, when cultured in a selective medium which contains an inhibitor of glutamine synthetase, such as methionine sulfoximine (MSX), but not glutamine. But when the mammalian cells have been introduced with an expression vector incorporated with glutamine synthetase, the cells become to be capable to grow in the presence of MSX at higher concentrations. At this time, if the cells are successively cultured while gradually increasing the concentration of the MSX, the result is that the cells capable of proliferating in the presence of the MSX at relatively higher concentrations are obtained. The selected cells selected as such a manner generally tend to express, at high levels, a gene encoding a protein of interest incorporated in the expression vector concomitantly with glutamine synthetase, as a result, mammalian cell thus will be obtained that express the protein of interest at high levels.

As a selection marker, dihydrofolate reductase (DHFR) may also be used. When DHFR is used as the selection marker, mammalian cells are cultured in a selective medium which contains a DHFR inhibitor such as methotrexate and aminopterin. If the cells have been successively cultured while gradually increasing the concentration of the DHFR inhibitor, the cells that can proliferate in the presence of the DHFR inhibitor at relatively higher concentrations are obtained. The selected cells selected as such a manner generally tend to express, at high levels, a gene encoding a protein of interest incorporated in the expression vector concomitantly with DHFR, as a result, mammalian cell thus will be obtained that express the protein of interest at high levels.

An expression vector has been known in which glutamine synthetase (GS), as a selection marker, is located downstream of a gene encoding a protein of interest via internal ribosome entry site (IRES), (International Patent Gazette; WO2012/063799, WO2013/161958). Expression vectors described in these literatures may be particularly preferable for the use in the method of production of the present invention.

For examples, an expression vector for expression of a protein can be preferably used in the method for production of the present inventions, that vector comprises a gene expression regulatory site, and a gene encoding the protein downstream thereof, an internal ribosome entry site further downstream thereof, a gene encoding a glutamine synthetase still further downstream thereof, and additionally a dihydrofolate reductase gene or a drug resistance gene downstream of either the same gene expression regulatory site or another gene expression regulatory site in addition to the former. In this expression vector, as a gene expression regulatory site or another gene expression regulatory site, a cytomegalovirus-derived promoter, an SV40 early promoter, a human elongation factor-1 alpha promoter (hEF-1 alpha promoter), and a human ubiquitin C promoter are preferable, and the hEF-1 alpha promoter is particularly preferable.

As an internal ribosome entry site, those derived from 5' untranslated regions of viruses or genes selected from the group consisting of viruses of Picornaviridae, Picornaviridae Aphthovirus, hepatitis A virus, hepatitis C virus, coronavirus, bovine enterovirus, Theiler's murine encephalomyelitis virus, Coxsackie B virus, human immunoglobulin heavy chain binding protein gene, *drosophila* antennapedia gene, and *drosophila* Ultrabithorax gene may be preferably used. The internal ribosome entry site derived from 5' untranslated regions of mouse encephalomyocarditis virus may be particularly preferably used. When an internal ribosome binding site derived from the 5' untranslated region of the mouse encephalomyocarditis virus is used, not only the wild type internal ribosome binding site, but also those of which part of the multiple start codons contained in the wild type internal ribosome binding site have been disrupted may be preferably used. Further, as a drug resistance gene to be preferably used in this expression vector, puromycin or neomycin resistance gene is preferable, and puromycin resistance gene is more preferable.

Further, for examples, an expression vector for expressing a protein can be preferably used in the method for production of the present inventions, that vector comprises human elongation factor-1 alpha promoter, and a gene encoding the protein downstream thereof, an internal ribosome entry site derived from 5' untranslated regions of mouse encephalomyocarditis virus further downstream thereof, a gene encoding a glutamine synthetase still further downstream thereof, and additionally a dihydrofolate reductase gene downstream of another gene expression regulatory site, wherein the internal ribosome binding site is that of which part of the multiple start codons contained in the wild type internal ribosome binding site have been disrupted. The expression vectors described in WO2013/161958 are the examples of such vectors.

Further, for examples, an expression vector for expressing a protein can be preferably used in the method for production of the present inventions, that vector comprises human elongation factor-1 alpha promoter, and a gene encoding the protein downstream thereof, an internal ribosome entry site derived from 5' untranslated regions of mouse encephalomyocarditis virus further downstream thereof, a gene encoding a glutamine synthetase still further downstream thereof, and additionally a drug resistance gene downstream of another gene expression regulatory site, wherein the internal ribosome binding site is that of which part of the multiple start codons contained in the wild type internal ribosome binding site have been disrupted. pE-mIRES-GS-puro described in WO2012/063799 and pE-mIRES-GS-mNeo described in WO2013/161958 are the examples of such vectors.

The internal ribosome entry site of the wild-type mouse encephalomyocarditis virus has three start codons (ATG) at or around its 3' end, whose sequence is set forth as SEQ ID NO:1 (5'-ATGataatATGgccacaaccATG-3'). The examples of an internal ribosome entry sites of which part of the initiation codons in the SEQ ID NO:1 have been disrupted include that having a nucleotide sequence set forth as SEQ ID NO:2 (5'-atgataagcttgccacaaccatg-3'). pE-mIRES-GS-puro and pE-mIRES-GS-mNeo described above are the expression vectors including the sequence set forth as SEQ ID NO:2, wherein part of the initiation codons have been disrupted.

In the present invention, mammalian cells into which an expression vector containing an incorporated gene encoding hDNase I are subjected to a selective culture in a selective medium to select cells expressing rhDNase I at high levels.

In performing a selective culture using DHFR as a selective marker, the concentration of the DHFR inhibitor in a selective medium is increased in a stepwise manner. When the DHFR inhibitor is methotrexate, the maximum concentration is preferably 0.25 to 5 μM, more preferably 0.5 to 1.5 μM, still more preferably about 1.0 μM.

When GS used as a selection marker, the concentration of the GS inhibitor in a selective medium is increased in a stepwise manner. When the GS inhibitor is MSX, the maximum concentration is preferably 100 to 1000 μM, more preferably 200 to 500 μM, and still more preferably about 300 μM. And performing this, a medium not containing glutamine is generally used as the selective medium.

When using an enzyme degrading puromycin as a selection marker, the maximum concentration of puromycin contained in a selective medium is preferably 3 to 30 μg/mL, more preferably 5 to 20 μg/mL, and still more preferably about 10 μg/mL.

When using an enzyme degrading neomycin as a selection marker, the maximum concentration of G418 contained in a selective medium is preferably 0.1 to 2 mg/mL, more preferably 0.5 to 1.5 mg/mL, and still more preferably about 1 mg/mL.

In addition, as a medium for culturing mammalian cells, both the medium used for selective culture and the medium used for producing rhDNase I (rhDNase I-production medium), both described later in detail, any medium can be used without particular limitation, as long as they can be used for culturing and growing mammalian cells, but a serum-free medium is preferably used.

Cells selected by selective culture and showing a high expression level of rhDNase I are used to produce rhDNase I as rhDNase I-producing cells. Production of rhDNase I is carried out by culturing the rhDNase I-producing cells in rhDNase I-production medium. This culture is called production culture.

In the present invention, an example of serum-free media which is to be used as rhDNase I-production medium is the medium which contains; 3 to 700 mg/mL of amino acids, 0.001 to 50 mg/L of vitamins, 0.3 to 10 g/L of monosaccharides, 0.1 to 10000 mg/L of inorganic salts, 0.001 to 0.1 mg/L of trace elements, 0.1 to 50 mg/L of nucleosides, 0.001 to 10 mg/L of fatty acids, 0.01 to 1 mg/L of biotin, 0.1 to 20 micrograms/L of hydrocortisone, 0.1 to 20 mg/L of insulin, 0.1 to 10 mg/L of vitamin $B_{12}$, 0.01 to 1 mg/L of putrescine, 10 to 500 mg/L of sodium pyruvate, and water-soluble iron compounds. As desired, it may also include thymidine, hypoxanthine, a conventional pH indicator, and antibiotics.

Further, DMEM/F12 medium, a mixed medium consisting of DMEM and F12, may also be used as a basic serum-free medium for rhDNase I production. Both of these media are well known to those skilled in the art. Furthermore, as a serum-free medium, DMEM(HG)HAM modified (R5) medium may be used, too, which contains sodium hydrogen carbonate, L-glutamine, D-glucose, insulin, sodium selenite, diaminobutane, hydrocortisone, ferric (II) sulfate, asparagine, aspartic acid, serine, and polyvinyl alcohol. Furthermore, a commercially available serum-free medium may also be used as a basic medium, including CD OptiCHO™ medium, CHO—S—SFM II medium, CD CHO medium (Life technologies Inc.), IS CHO-V™ medium (Irvine Scientific Inc.), EX-CELL™ 302 medium, or EX-CELL™ 325-PF medium (SAFC Biosciences Inc).

In the production culture of hDNase I-producing cells, the density of the rhDNase I-producing cells in the medium for rhDNase I production is preferably adjusted to $0.2 \times 10^5$ to $5 \times 10^5$ cells/mL, more preferably $1 \times 10^5$ to $4 \times 10^5$ cells/mL, still more preferably about $2 \times 10^5$ cells/mL when starting the culture. Production culture has been performed while observing the cell viability (%) over time, so that the cell survival rate during the production culture is maintained preferably at 85% or more, more preferably 90% or more.

During the production culture, the culture temperature is maintained preferably at 35 to 37.5° C., more preferably at 37° C., and the dissolved oxygen saturation level during the production medium is maintained preferably at 58 to 62%, more preferably at about 60%. Here, the term "dissolved oxygen saturation level" means the dissolution amount of oxygen when the saturated dissolution amount of oxygen is taken as 100% under same conditions.

During the production culture, the production medium is stirred with an impeller (impeller). At this time, the rotational speed of the impeller is adjusted preferably to 67 to 72 rotations per minute, more preferably to 70 rotations per minute, but the rotational speed may be changed as needed depending on the shape of the impeller or the like.

Suitable culture conditions for the production culture include, for example, such a condition in that the density of the rhDNase I-producing cells in the medium for rhDNase I production at the start of the production culture is $2 \times 10^5$ cells/mL; the culture temperature during the production culture period is maintained at 37° C.; the dissolved oxygen saturation in the production medium is 60%; oxygen is provided in the production medium at the rate of 31.25 mL/min per liter of the medium; air and $CO_2$ are provided respectively at the rate of 125 mL/min and 37.5 mL/min; and the medium is agitated with an impeller rotating at a speed of 70 rpm.

In the production culture, rhDNase I is secreted from the rhDNase I-producing cells and accumulates in the medium. The production culture has been conducted until the concentration of rhDNase I in the medium reaches preferably 400 mg/L or more, more preferably 550 mg/L or more, still more preferably 700 mg/L or more. The culture period of the cells in the production culture is preferably 8 to 16 days, more preferably 10 to 14 days, still more preferably 11 to 14 days.

The rhDNase I accumulated in the culture medium in the production culture is purified by processes using various chromatographies. Each one of chromatography for purifying rhDNase I may be conducted under the presence of a nonionic surfactant in order to prevent nonspecific adsorption of proteins according to the circumstance. There is no particular limitation as for the nonionic surfactant, but preferably a polysorbate type surfactant, more preferably polysorbate 80, and still more preferably polysorbate 80 is used. The concentration of the nonionic surfactant is preferably 0.005% (w/v) to 0.015% (w/v), more preferably 0.01% (w/v).

Purification process of rhDNase I can be carried out under room temperature or low temperature environment, but carried out preferably under a low temperature environment, and particularly preferably at a temperature of 1 to 10° C.

The first step of the purification process is an anion exchange chromatography. Though there is no particular limitation as to the anion exchange resin used in this step, but a strong anion exchange resin is preferred, and those having a trimethylammonium group are particularly preferred. In the first step, rhDNase I is let bind to an anion exchange resin equilibrated with a buffer having pH near neutral and containing salts and calcium ions. The buffer used in this step is preferably a Tris-HCl buffer solution, and the pH thereof is preferably 7.2 to 7.8, and more preferably about 7.5. Though there is no particular limitation as to the salt contained in the buffer, but sodium chloride is preferred, and the concentration thereof is preferably 30 to 70 mM, and more preferably about 50 mM. Further, the concentration of calcium ion contained in the buffer is preferably 0.1 to 10 mM, more preferably 0.5 to 2.0 mM, and still more preferably 0.8 to 1.2 mM, particularly preferably about 1.0 mM.

After washing the column to which rhDNase I binds, rhDNase I is eluted from the column using an acidic buffer containing salts and calcium irons, and the fractions containing rhDNase I are collected. The acid buffer used for this is preferably an acetate buffer, and the pH thereof is preferably 4.0 to 5.0, more preferably 4.2 to 4.8, further more preferably about 4.5. Though there is no particular limitation as to the salts contained in the buffer, but sodium chloride is preferable, and the concentration thereof is preferably 170 to 230 mM, more preferably 190 to 210 mM, and further more preferably about 200 mM. And the concentration of calcium irons in the buffer is preferably 0.1 to 10 mM, more preferably 0.5 to 2.0 mM, further more preferably 0.8 to 1.2 mM, and particularly preferably is about 1.0 mM.

The second step of the purification process is a column chromatography employing as solid phase a material having affinity for phosphate group. Though there is no particular limitation as to the solid phase having affinity for phosphate group in this process, but hydroxyapatite and fluoroapatite may be preferable, and hydroxyapatite may be particularly preferable. Prior to being loaded on the column chromatography employed in the second step, the pH of the eluate collected in the first step, which contains rhDNase I, has been adjusted preferably 6.2 to 6.8, and more preferably about 6.5.

In the second step of the purification process, rhDNase I is let bind to the solid phase equilibrated with a buffer of pH near neutral containing salts and calcium ions. The buffer used in this process is preferably a MES buffer, and the pH thereof is preferably 6.2 to 6.8, and more preferably about 6.5. And though there is no particular limitation as to the salt contained in the buffer, but sodium chloride is preferable, and the concentration thereof is preferably 70 to 130 mM, more preferably 90 to 110 mM, and still more preferably about 100 mM. And the concentration of calcium iron contained in the buffer is preferably 0.2 to 2.0 mM, more preferably 0.5 to 1.5 mM, and still more preferably about 1.0 mM.

After washing the column to which rhDNase I binds, rhDNase I is eluted from the column with a buffer having a pH near neutral and containing salts and calcium ions, and the fractions containing rhDNase I are collected. The buffer used in this is preferably a MES buffer, and the pH thereof is preferably 6.2 to 6.8, and more preferably about 6.5. And the concentration of phosphate ion contained in the buffer is preferably 10 to 20 mM, more preferably 13 to 17 mM, and still more preferably about 15 mM. And the concentration of calcium iron contained in the buffer is preferably 0.2 to 1.0 mM, more preferably 0.4 to 0.6 mM, and more preferably about 0.5 mM.

The third step of the purification process is a cation exchange column chromatography. Though there is no particular limitation as to a cation exchange resin used in this process, but a strong cation exchange resin is preferable, and those having sulfo group is particularly preferable. Prior to being loaded on the column chromatography employed in the third step, the pH of the eluate collected in the second step, which contains rhDNase I, has been adjusted preferably 4.2 to 4.8, and more preferably about 4.5.

In the third step of the purification process, rhDNase I is let bind to the cation exchange resin equilibrated with an acidic buffer containing salts and calcium ions. The buffer used in this process is preferably an acetate buffer, and the pH thereof is preferably 4.2 to 4.8, and more preferably about 4.5. And though there is no particular limitation as to the salt contained in the buffer, but sodium chloride is preferable, and the concentration thereof is preferably 10 to 20 mM, more preferably 12 to 18 mM, and still more preferably about 15 mM. And the concentration of calcium iron contained in the buffer is preferably 2 to 20 mM, more preferably 5 to 15 mM, and still more preferably 8 to 12 mM, and particularly preferably about 10 mM.

After washing the column to which rhDNase I binds, rhDNase I is eluted from the column with a buffer having a pH near neutral and containing salts and calcium ions, and the fractions containing rhDNase I are collected. The buffer used in this is preferably a HEPES buffer, and the pH thereof is preferably 6.7 to 7.8, and more preferably about 7.0 to 7.5. And though there is no particular limitation as to the salts contained in the buffer, but sodium chloride is preferable, and the concentration thereof is 40 to 70 mM, more preferably to 55 mM, still more preferably about 50 mM. And the concentration of calcium iron contained in the buffer is preferably 2 to 20 mM, more preferably 5 to 15 mM, still more preferably 8 to 12 mM, and particularly preferably about 10 mM.

The forth step of the purification process is dye ligand affinity chromatography. The dye ligand affinity resin used in this process is a resin conjugated with a dye. Though there is no particular limitation as to the dye to let conjugated to the resin, but triazine dye is preferably used, and a blue triazine dye such as Cibacron™ Blue F3GA is particularly preferably used. For example, Blue Sepharose 6 FF (Fast Flow, GE Healthcare) shown in the following schematic formula (I), therein dye Cibacron™ Blue F3GA has been covalently conjugated to Sepharose, is preferable as the resin used in the forth step of the purification process.

[Chem. 1]

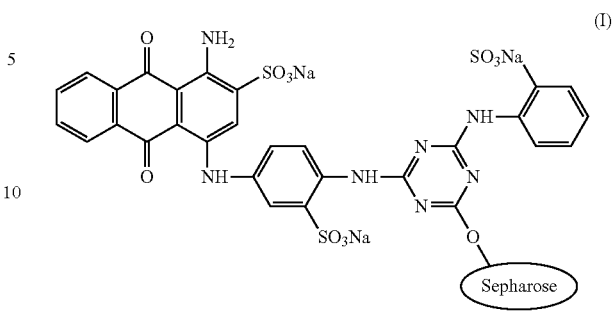

Prior to being loaded on the column chromatography employed in the forth step, the pH of the eluate collected in the third step, which contains rhDNase I, has been adjusted preferably 4.2 to 4.8, and more preferably about 4.5.

In the forth step of the purification process, rhDNase I is let bind to the dye affinity column equilibrated with an acidic buffer containing salts and calcium ions. The buffer used in this is preferably an acetate buffer, and the pH thereof is preferably 4.2 to 4.8, and more preferably about 4.5. And though there is no particular limitation as to the salts contained in the buffer, sodium chloride is preferable, and the concentration thereof is preferably 60 to 80 mM, more preferably 65 to 75 mM, and still more preferably about 70 mM. And the concentration of calcium iron contained in the buffer is preferably 0.2 to 2 mM, more preferably 0.5 to 1.5 mM, and still more preferably about 1.0 mM.

After washing the column to which rhDNase I binds, rhDNase I is eluted from the column with a buffer having a pH near neutral and containing salts and calcium ions, and the fractions containing rhDNase I are collected. The buffer used in this is preferably a MES buffer, and the pH thereof is preferably 6.2 to 6.8, and more preferably about 6.5. And though there is no particular limitation as to the salts contained in the buffer, but sodium chloride is preferable, and the concentration thereof is 80 to 120 mM, more preferably 90 to 110 mM, still more preferably about 100 mM. And the concentration of calcium iron contained in the buffer is preferably 2 to 20 mM, more preferably 5 to 15 mM, and still more preferably about 10 mM.

As the fifth step of the purification process, purification step using a gel filtration column chromatography can be additionally employed as needed. The gel filtration column chromatography is the step for removing multimeric complexes or decomposition products of rhDNase I as well as low molecular-weight impurities such as endotoxins from rhDNase I. Such a procedure has been well known.

The purity of rhDNase I obtained by the production method of the present invention is 95% or more, and its specific activity is preferably 920 U/mg or more, more preferably 950 U/mg or more, still more preferably 960 U/mg or more, and still more preferably 970 U/mg or more. Therefore, as a standard value for a drug substance of rhDNase I, which was produced using the rhDNase I obtained by the production method of the present invention, its specific activity can be properly set to 920 to 1000 U/mg, 950 to 1000 U/mg, 960 to 1000 U/mg, 970 to 1000 U/mg, and the like.

One unit of the enzymatic activity of rhDNase I (Kunitz unit) has been defined as corresponding to the enzymatic activity which, when the reaction is performed at 25° C. by adding rhDNase I to a salmon sperm-derived DNA solution dissolved in a 0.1 M acetate buffer (pH 5.0) at a concentration of 1 mg/mL, increases absorbance at 260 nm (OD260) of the solution at the rate of 0.001 per minute. Kunitz unit is established by Kunitz et., al. (Kunitz M J. Gen Physiol. 33. 349-362 (1950)). The value obtained by subtracting OD492 from OD620 measured by DNA-methyl green assay described in example 9 is correlated with the activity value as defined in such a manner. Therefore, the activity can be determined by obtaining the calibration curve by DNA-methyl green assay using rhDNase I solution of a known activity value as a standard, and interpolating into this a measured value of rhDNase I solution to be desired.

As needed, a step for virus inactivation can optionally be added to the manufacturing process of the present invention. Though there is no particular limitation as to which virus inactivation process is to be employed, a solvent-surfactant method may be preferably employed. For this purpose, a nonionic surfactant is added to a solution containing rhDNase I, and the mixed solution has been incubated for more than 3 hours. Though there is no particular limitation as to which nonionic surfactant is to be employed, polysorbate 20, polysorbate 80, and tri-(n-butyl) phosphate alone or any combinations thereof preferably, and more preferably a combination of polysorbate 80 and tri-(n-butyl) phosphate may be employed. Such an additional step for virus inactivation can be introduced between any two adjacent steps in the production process of rhDNase I.

EXAMPLES

Though the present invention will be described in further detail below with reference to an example, it is not intended that the present invention be limited to the example.

Example 1: Construction of a Vector for Expression of rhDNase I

A DNA fragment containing a gene encoding full length of natural-type human DNase I was chemically synthesized (SEQ ID NO: 3). This DNA fragment was digested with MluI and NotI, and inserted into a vector for expression in mammalian cells (pE-mIRES-GS-puro). This rhDNase I expression vector has been designated as pE-mIRES-GS-puro/DRNI (FIG. 1), and used in experiments below. As pE-mIRES-GS-puro, used was what had been constructed by a method described in international patent gazette (WO2012/063799). Although the DNA represented by SEQ ID NO:3 encodes a peptide chain consisting of 282 amino acids (SEQ ID NO:4), but a peptide consisting of 260 amino acids, which is a remnant when a leader peptide consisting of N-terminal 22 amino acids is removed from the peptide chain, corresponds to rhDNase I.

Example 2: Introduction of the Vector for Expression of rhDNase I into Cells

The vector for expression of rhDNase I constructed in the Example 1 (pE-mIRES-GS-puro/DRNI) was linearized by digestion with AseI, and then, introduced into CHO-K1 cells by electroporation method or lipofection method to transform the cells. Cell culture after transformation was performed by using CD-OptiCHO™ medium (Life technologies Inc.) supplemented with HT supplement 100×(Life technologies Inc.) at a volume of 1/100 (v/v) as a basal medium. This basal medium does not contain glutamine.

In summary, the electroporation method was carried out by the following method. CHO-K1 cells were suspended in Opti-MEMI medium (Life technologies Inc.), so that the cell density became $5\times10^6$ cells/mL. 100 μL of this suspending solution was taken and 0.5 to 1.0 μg of the above linearized expression vector was added to the solution. After mixing, the whole amount of the solution was transferred to an electrode-attached cuvette (distance between electrodes; 2 mm), and to the solution an electric pulse (voltage; 160V, pulse width; 15 msec.) was applied once by using an electroporation apparatus (Gene Pulser Xcell™, BioRad Co.). And then, 1 mL of the basal medium supplemented with 4 mM of glutamine was added to the cuvette. After mixing, the whole amount was transferred to a well of a 24-well plate and cultured in the presence of 5% $CO_2$ at 37° C. for about 24 hours. And then, the cells in the well were collected by centrifugation, suspended with the basal medium containing 30 μM of MSX, and transferred to a new well of a 24-well plate.

In summary, the lipofection method was carried out by the following method. CHO-K1 cells were suspended in Opti-MEMI medium (Life technologies Inc.), so that the cell density became $5\times10^6$ cells/mL. 100 μL of this suspending solution was taken and added to a 24-well plate in which 480 μL of the basal medium had been added in advance. 0.5 to 1.0 μg of the above linearized expression vector was added to 30 μL of Opti-MEMI medium, and further to this, 4 μL of HilyMax (gene transfer reagent, Dojindo Co.) was added. After mixing to make a mixture, the mixture was stand for 15 minutes at room temperature. Whole amount of this mixture was added to the well of the 24-well plate added with the cells. After mixing, the cells were cultured in the presence of 5% $CO_2$ at 37° C. for about 24 hours. And then, the cells in the well were collected by centrifugation, suspended with the basal medium containing 30 μM of MSX, and transferred to a new well of a 24-well plate.

Example 3: Bulk Culture of the Cells Introduced with the Vector for Expression of rhDNase I Selection culture was started using CD-OptiCHO™ medium containing 30 μM of MSX for the cells which were transferred to the new well of the 24-well plate after introduced with the vector for expression of rhDNase I by electroporation or lipofection method. Cells with high tolerance to MSX were obtained while gradually increasing the concentration of MSX every few weeks and finally culturing in a CD-OptiCHO™ medium containing 300 μM of MSX and 5 μg/mL of puromycin. These cells were designated bulk cells and the above culture process to obtain the bulk cells was designated as bulk culture.

As the enzymatic activity of rhDNase I was shown to be 120 U/mL in the culture supernatant of the bulk cells obtained by electroporation method when the enzymatic activity was measured by a method for measurement of the enzymatic activity as described later, these bulk cells were used in later experiments.

Example 4: Cloning of rhDNase I-Producing Cells

The bulk cells obtained in Example 3 above were suspended in a basic medium containing 300 μM of MSX and 10 μg/mL of puromycin to prepare a cell suspension, and 200 μL of this cell suspension was seeded on each well of a 96-well plate in such a manner that approximately one cell might be seeded per well. At this time, as feeder cells, CHO-K1 cells which has not been introduced with the expression vector were made included in the number of $1\times10^4$ cells per well. Colony formation of each well was confirmed on the 14th day of culture, the culture supernatant of the well in which a single colony was formed was collected, and the enzymatic activity of rhDNase I in the culture supernatant was measured by a method for measurement of the enzymatic activity as described later. And 52 wells were selected which contained culture supernatants showing high enzymatic activities. The cells in the selected wells were seeded in each well of a 24-well plate and cultured, and cells in a well showing the highest enzymatic activity were finally selected.

Subsequently, the cells in the selected well were collected, and the collected cells were suspended in a basic medium containing 300 μM of MSX and 10 μg/mL of puromycin to prepare a cell suspension, and 200 μL of this cell suspension was seeded on each well of a 96-well plate in such a manner that approximately one cell might be seeded per well. At this time, as feeder cells, CHO-K1 cells which has not been introduced with the expression vector were made included in the number of $1 \times 10^4$ cells per well. Colony formation of each well was confirmed on the 14th day of culture, and the culture supernatant of the well in which a single colony was formed was collected, and the enzymatic activity of rhDNase I in the culture supernatant was measured by a method for measurement of the enzymatic activity as described later. And 70 wells were selected which contained culture supernatant showing high enzymatic activity. The cells in the selected wells were seeded in each well of a 24-well plate and cultured, and cells in a well showing the highest enzymatic activity were finally selected.

Subsequently, the cells are collected from the selected well, and the same operation as described above is repeated once to select one well containing the culture supernatant showing the highest enzymatic activity, and cells are collected from this well. The collected cells were used as rhDNase I-producing cells in the following experiments.

Example 5: Production Culture of rhDNase I-Producing Cells

The rhDNase I-producing cells obtained in Example 4 were subjected to stepwise expansion culture, and finally cells were suspended in 800 mL of medium at a density of $2 \times 10^5$ cells/mL. This cell suspension was added to a 1 L chamber of a bioreactor (Single-Use Bioreactor, Thermo Fisher Scientific Inc.) set to the conditions shown in Table 1, and the cells were cultured for 14 days. During the culture period, a feed solution comprising 50 ml of Efficient feed kit A and 50 ml of Efficient feed kit B was added to the chamber on the 4th, 7th, and 10th day after starting the culture. Here, the expansion culture and the production culture were carried out using a CD-OptiCHO™ medium containing 20 μg/mL of insulin and supplemented with HT supplement 100× in an amount of 1/100 (v/v).

TABLE 1

| Setting conditions of bioreactor | |
| --- | --- |
| Chamber Volume | 1 L |
| Medium volume (at the start of culture) | 800 mL |
| Rotation speed of impeller | 70 rpm |
| Culture temperature | 37° C. |
| pH | 7.2 |
| Dissolved oxygen saturation level | 60% |
| Aeration (in medium) | 25 mL ($O_2$)/min |

TABLE 1-continued

| Setting conditions of bioreactor | |
| --- | --- |
| Aeration (surface of medium) | 100 mL (Air)/min |
| Aeration (surface of medium) | 30 mL ($CO_2$)/min |
| Feed | $4^{th}$, $7^{th}$, and $10^{th}$ day after starting the culture |

Figure 2:
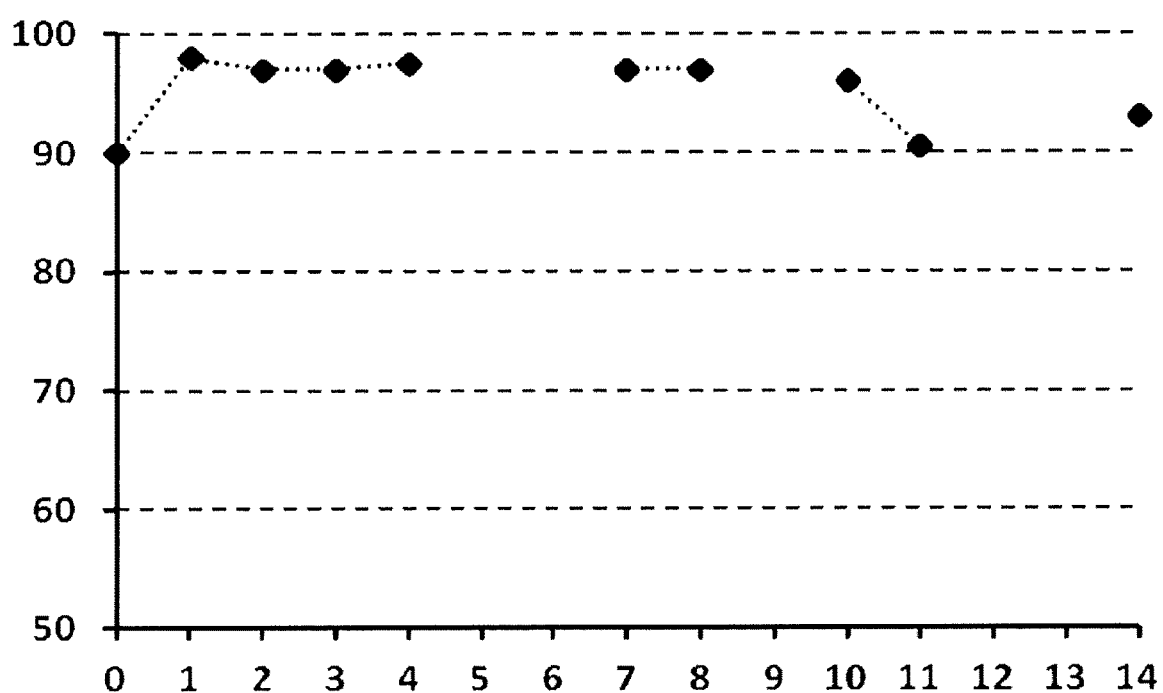
FIG. 2 shows cell survival rate of rhDNase I-producing cells in the course of the production culture of the cells. Vertical and horizontal axis indicates the cell survival rate (%) and culture days, respectively.
Figure 3:
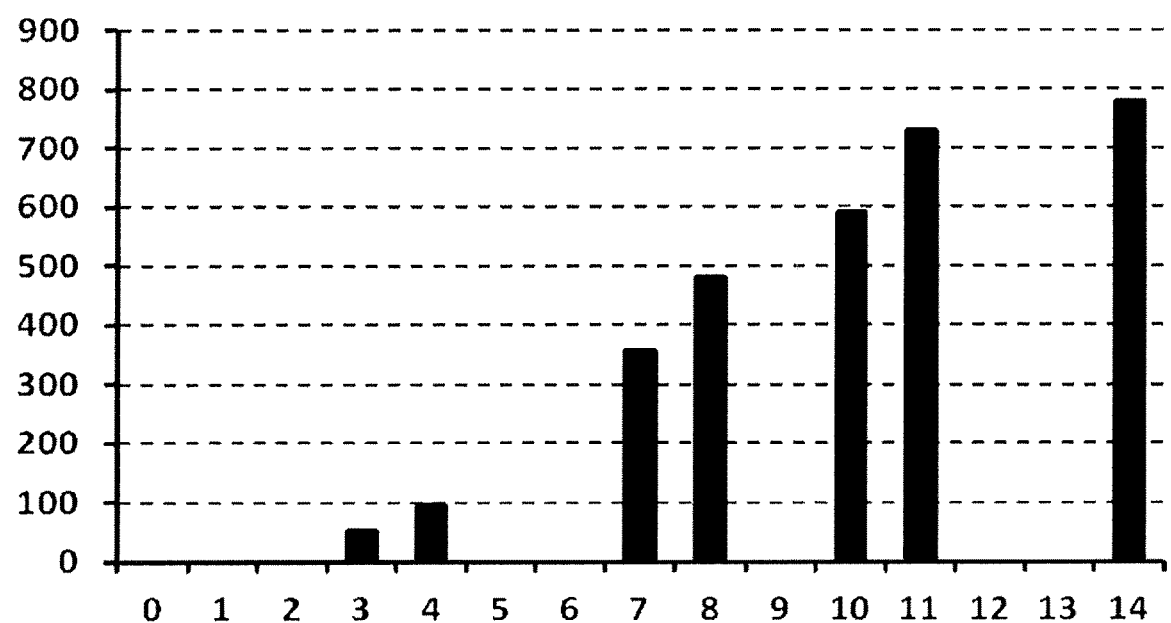
FIG. 3 shows concentration of rhDNase I in the medium in the course of the production culture of the cells. Vertical and horizontal axis indicates the concentration of rhDNase I (mg/L) and culture days, respectively.

During the culture period, the cell viability and the amount of rhDNase I contained in the medium were measured over time. The amount of rhDNase I was measured by an ELISA method described below. During the culture period, the viability of the cells was constantly kept at 90% or more, which indicates that the setting conditions of the bioreactor shown in Table 1 are suitable for the culturing condition of rhDNase I-producing cells (FIG. 2). Further, the amount of rhDNase I contained in the medium increased rapidly until the 11th day after starting the culture and reached 728 mg/L on the 11th day after starting the culture (FIG. 3). After that, the amount of rhDNase I contained in the medium further increased and reached 778 mg/L on the 14th day after starting the culture (FIG. 3). That is, by introducing the vector for expression of rhDNase I shown in Example 2 into CHO cells, and incubating rhDNase I-producing cells selected by the selective culture under the setting conditions of the bioreactor shown in Table 1, it has been found that rhDNase I is able to be obtained in the medium at an extremely high expression level.

Example 6: Purification of rhDNase I

After completion of the production culture, the medium was collected and filtrated through a membrane filter (pore size; 0.22 μm, Millipore Inc.) to obtain a culture supernatant. 75 mL of the culture supernatant was taken and diluted by adding an equal volume of 20 mM Tris buffer (pH 7.5) containing 1 mM $CaCl_2$. The dilution of the culture supernatant was applied to an anion exchange column, NuviaQ media (column volume; 5 mL, bed height; 25 cm, BioRad Inc.), equilibrated with 2-fold column volume of 20 mM Tris buffer (pH 7.5) containing 50 mM NaCl and 1 mM $CaCl_2$ at a flow rate of 1.8 mL/min to let rhDNase I be adsorbed to the resin. Subsequently, at the same flow rate, after washing the column with 6-fold column volume of 40 mM acetate buffer (pH 5.0) containing 1 mM $CaCl_2$, rhDNase I was eluted from the column with 6-fold column volume of 40 mM acetate buffer (pH 4.5) containing 200 mM NaCl and 1 mM $CaCl_2$.

The pH of the above eluted fractions from the anion exchange column was adjusted to 6.5 by adding 1M Tris buffer (pH 8.0). The pH-adjusted eluted fractions were applied to a hydroxyapatite column, Bio-Scale Mini CHT Type I Cartridge (column volume; 5 mL, BioRad Inc.), equilibrated with 2-fold column volume of 20 mM MES (pH 6.5) containing 100 mM NaCl and 1 mM $CaCl_2$ to let rhDNase I be adsorbed to the solid phase. Subsequently, at a flow rate of 2.5 mL/min, after washing the column with 5-fold column volume of 20 mM MES buffer (pH 6.5) containing 0.5 mM $CaCl_2$, rhDNase I was eluted from the column with 6-fold column volume of 20 mM MES buffer (pH 6.5) containing 15 mM $KH_2PO_4$ and 0.5 mM $CaCl_2$.

The pH of the above eluted fractions from the hydroxyapatite column was adjusted to 4.5 by adding acetic acid. The pH-adjusted eluted fractions were applied to a cation exchange column, Fractogel™ EMD $SO_3^-$ (M) (column volume; 5 mL, bed height; 25 cm, Merck Inc.), equilibrated with 2-fold column volume of 40 mM acetate buffer (pH 4.5) containing 15 mM NaCl and 10 mM $CaCl_2$ at a flow rate of 1.8 mL/min to let rhDNase I be adsorbed to the carrier. Subsequently, at the same flow rate, after washing column with 5-fold column volume of 40 mM acetate buffer (pH 4.5) containing 15 mM NaCl and 10 mM $CaCl_2$, rhDNase I was eluted from the column with 6-fold column volume of 20 mM HEPES buffer (pH 7.0) containing 50 mM NaCl and 10 mM $CaCl_2$, and further eluted from the column with 6-fold column volume of 20 mM HEPES buffer (pH 7.5) containing 50 mM NaCl and 10 mM $CaCl_2$.

The pH of the above eluted fractions from the cation exchange column was adjusted to 4.5 by adding acetic acid. The pH-adjusted eluted fractions were applied to a dye ligand affinity column, HiScreen Blue Sepharose FF (column volume; 4.7 mL, GE Healthcare Inc.), equilibrated with 2-fold column volume of 40 mM acetate buffer (pH 4.5) containing 70 mM NaCl and 1 mM $CaCl_2$ at a flow rate of 1.8 mL/min to let rhDNase I be adsorbed to the resin. Subsequently, at the same flow rate, after washing column with 5-fold column volume of 40 mM acetate buffer (pH 4.5) containing 70 mM NaCl and 1 mM $CaCl_2$, rhDNase I was eluted from the column with 6-fold column volume of 20 mM MES buffer (pH 6.5) containing 100 mM NaCl and 1 mM $CaCl_2$. The rhDNase I eluted herein was designated as rhDNase I-purified product.

As a result of quantifying rhDNase I contained in the culture supernatant used for the purification of rhDNase I and that contained in the rhDNase I-purified product by ELISA method described below, about 72% of the rhDNase I contained in the culture supernatant at the start of the purification has been shown to be recovered as the rhDNase I-purified product. These results indicate that the rhDNase I purification method described above is extremely efficient as a purification method of rhDNase I with little loss of rhDNase I in the purification process.

Example 7: Production of Anti-rhDNase I Antibodies

The bulk cells obtained in Example 3 as described above were suspended with CD-OptiCHO™ medium containing 4 mM glutamine at a density of $2 \times 10^5$ cells/mL so that the total volume became 240 mL. 30 mL of this cell suspension was dispensed into 8 dishes with 15 cm diameter, and incubated for 5 days under the existence of 5% $CO_2$ at 37° C. After incubation, the medium was collected and filtrated by a filter membrane (pore size; 0.22 μm, Millipore Inc.) to obtain a culture supernatant. An equal volume of 1 mM $CaCl_2$ solution was added to 220 mL of the culture supernatant. After mixing, half volume thereof was applied to an anion exchange column, HiTrap Capto Q (column volume; 5 mL, GE Healthcare Inc.) at a flow rate of 3 mL/min to let rhDNase I be adsorbed to the resin. Subsequently, at the same flow rate, washing was conducted with 5-fold column volume of 20 mM MES buffer (pH 6.5) containing 50 mM NaCl and 1 mM $CaCl_2$. Subsequently, at the same flow rate, rhDNase I was eluted from the column with 30-fold column volume of elution buffer by a linear concentration gradient, wherein an elution buffer A was 100% at a start of elution and elution buffer B was 100% at the end of elution, and wherein the elution buffer A was 20 mM MES buffer (pH 6.5) containing 50 mM NaCl and 1 mM $CaCl_2$, and the elution buffer B was 20 mM MES buffer (pH 6.5) containing 300 mM NaCl and 1 mM $CaCl_2$. The remaining half volume was also purified by the anion exchange column chromatography in the same manner. Fractions containing rhDNase I were collected and concentrated to a volume of 1.5 mL using Amicon Ultra 10 K to obtain a concentrated solution of rhDNase I.

The above concentrated solution was loaded on a gel filtration column, HiLaod 16/60 Superdex75 (GE Healthcare Inc.), equilibrated with 10 mM MES buffer (pH 6.3) containing 150 mM NaCl, 1 mM $CaCl_2$, and 0.05% Tween 80, at a flow rate of 1.0 mL/min. Subsequently, the gel filtration was continued at the same flow rate and with the same buffer, and fractions containing rhDNase I were collected to obtain a crudely purified product of rhDNase I. Using this crudely purified product of rhDNase I as an antigen, two rabbit (New Zealand white) has been immunized. Immunization has been conducted by subcutaneous injection of 0.2 mg of the crudely purified product of rhDNase I to the rabbits at one time and in total four times at intervals of 2 to 4 weeks. Freund's Complete Adjuvant was used in the first immunization, and Freund's Incomplete Adjuvant was used in the subsequent immunizations. Rabbit anti-hDNase I antibody was obtained by purifying rabbit anti-hDNase I antibody from the serum of the immunized rabbits by a standard technique. Further a part of the obtained rabbit anti-hDNase I antibody was labeled using an HRP labeling kit (Dojindo Co.) to prepare HRP-labeled anti-hDNase I antibody.

Example 8: Quantification of rhDNase I (ELISA Method)

An HRP-labeled anti-hDNase I antibody solution was prepared by diluting the HRP-labeled anti-hDNase I antibody prepared in Example 7 above to a concentration of 0.0625 μg/mL with TBS-T containing 0.1% BSA. An OPD solution was prepared by mixing 0.025 M citric acid solution with an equal volume of 0.05 M $NaHPO_4$ solution and adjusting the pH to 5.0. A substrate solution was prepared by dissolving o-phenyldiamine hydrochloride (OPD tablet, Wako Pure Chemical Co.) in the OPD solution at a concentration of 0.4 mg/mL and further to this adding $H_2O_2$ to be 0.0086%. And, rhDNase I (PROSPEC Inc.) diluted with TBS-T containing 0.1% BSA was used as a standard of rhDNase I.

The rabbit anti-hDNase I antibody prepared in Example 7 above was diluted with 0.05 M $NaHCO_3$ to adjust the concentration to 0.5 μg/mL. 100 μL of this antibody dilution was dispensed into each well of a 96-well plate and stand for one hour at 37° C. After removing the solution and washing each well with 300 μL of TBS-T once, 300 μL of TBS-T containing 1% BSA was added to each well and stand for 30 minutes at room temperature. After removing the solution, the standard of rhDNase I and the rhDNase I-purified product were added to each well and stand for one hour at room temperature. After removing the solution and washing each well with 300 μL of TES-T thrice, 100 μL of HRP-labeled anti-hDNase I antibody solution was added to each well and stand for one hour at room temperature. After removing the solution and washing each well with 300 μL of TBS-T thrice, 100 μL of the substrate solution was added to each well and stand for 10 minutes at room temperature. And after adding 100 μL of a reaction stopping solution, the absorbance at 260 nm of each well was measured by using a plate leader. A calibration curve was prepared from the measured value of the standard of rhDNase I, and then the measured value of the rhDNase 1-purified product was

Example 9: Measurement of Enzymatic Activity of rhDNase I (DNA-Methyl Green Assay)

0.2% DNA solution was prepared by adding salmon sperm DNA (Sigma-Aldrich) to 25 mM HEPES buffer (pH 7.5) containing 1 mM EDTA at a concentration of 2 mg/mL. A methyl green solution was prepared by dissolving methyl green powder (Sigma-Aldrich) in 20 mM acetic acid/NaOH (pH 4.2) at a concentration of 0.4 (w/v). A substrate solution was prepared by mixing the 0.2% DNA solution, the methyl green solution, and a dilution solution (25 mM HEPES (pH 7.5) containing 4 mM $CaCl_2$, 4 mM $MaCl_2$, 0.1% BSA, and 0.05% Tween20) at a ratio of 128:7.7:114, agitating overnight at room temperature, and filtrating by membrane filter (pore size; 0.22 μm, Corning Inc.). The substrate solution was stored in a frozen state and thawed before use.

A standard solution of rhDNase I was prepared by dissolving rhDNase I (PROSPEC Inc.) with the dilution solution at a concentration of 100 U/mL. This standard solution was diluted two-fold in the range of 1 U/mL to 0.0078 U/mL using the dilution solution to create a calibration curve. And, the rhDNase 1-purified product obtained in Example 6 was diluted with the dilution solution as desired.

100 μL of each of the dilutions of the standard solution of rhDNase 1 and the diluted rhDNase I-purified product described above were added to each well of a 96-well microtiter plate. After adding 100 μL of the substrate solution to each well and mixing, the reaction was performed for 3 hours at 30° C. by leaving stand. And then, the absorbance at 260 nm (OD260) and the absorbance at 492 nm (OD492) of each well were measured by using a plate leader. By preparing a calibration curve by subtracting OD492 from OD620, and therein interpolating the measured value of the purified product of rhDNase I, the activity of the purified product of rhDNase I was calculated.

The specific activity of rhDNase I was determined from the measured value of the activity of the purified product of rhDNase I and the concentration of the purified product of rhDNase I measured in Example 8. At this time, as a control, the specific activity of a commercially available medical rhDNase I (control product) was concomitantly measured. As a result, the specific activity of the purified product of rhDNase I and the control product was measured to be 974 U/mg and 950 U/mg, respectively, showing that the purified product of rhDNase I, at least depending on the production lot, has higher specific activity than the control product. These results indicate that the purity of the purified product of rhDNase I obtained in Example 6 reached to a level equivalent to commercially available rhDNase I for medical use.

Example 10: Measurement of Purity of rhDNase I (SDS-PAGE Electrophoresis)

Figure 4:
FIG. 4 shows a pattern obtained by SDS-PAGE electrophoresis of purified rhDNase I.

10 μL of the purified product of rhDNase I was mixed with an equal volume of a loading buffer (125 mM Tris buffer (pH 6.5) containing 4% SDS, 4% mercaptoethanol, and 8M urea). After heated at 10 minutes at 50° C., electrophoresis was carried out using a polyacrylamide gel (Super Sep™ Ace 10-20%, Wako Pure Chemical Inc.). After the electrophoresis, the gel was stained with Oriole stain. On the gel stained with Oriol stain, only a band derived from rhDNase I at a position corresponding to molecular weight 35 to 37 kD was able to be observed (FIG. 4).

Example 11: Measurement of Purity of rhDNase I (SE-HPLC)

Figure 5:
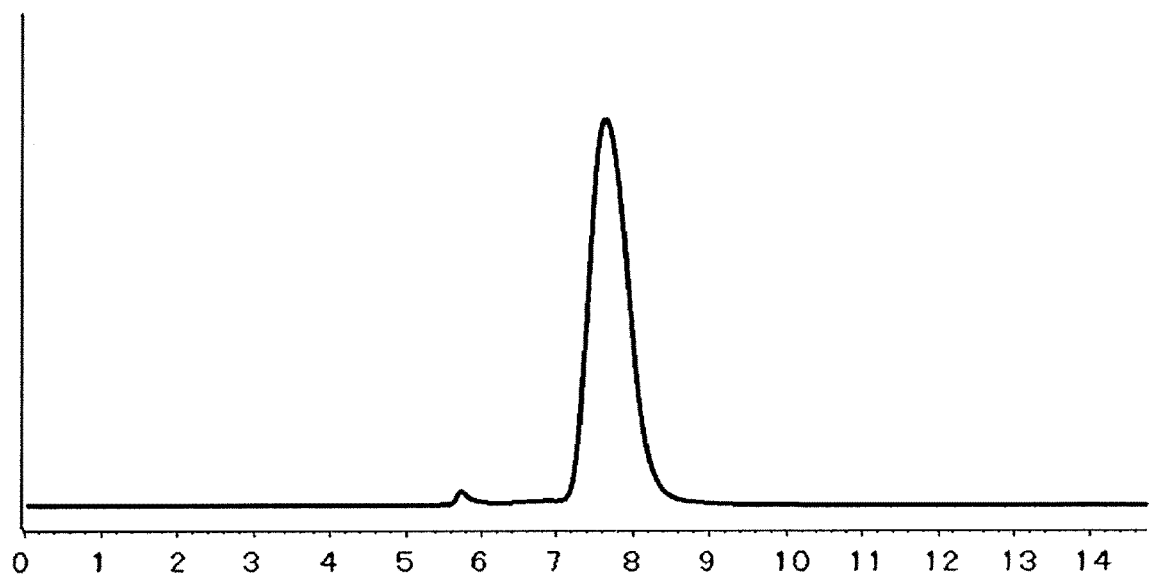
FIG. 5 shows a chart of SE-HPLC of purified rhDNase I. Vertical and horizontal axis indicates absorbance at 215 nm and retention time (min.), respectively

TSKgelG3000SWXL column (inner diameter 7.8 mm×30 cm, TOSOH Inc.) was set on LC-20A system, UV/VIS detector of SPD-20AV (SHimazu Co.). 10 μL of the purified product of rhDNase I was loaded on the column equilibrated with 25 mM phosphate buffer saline (PBS) at a flow rate of 0.5 mL/min. The elution profile was created by measuring the absorbance at 215 nm. There was almost only a single peak derived from rhDNase I in the obtained elution profile. (FIG. 5).

From the specific activity value, the pattern of SDS-PAGE electrophoresis, and the analytical result using SE-HPLC of the purified product of rhDNase I as described above, the purity of the rhDNase I-purified product has been shown to be more than 95%.

INDUSTRIAL APPLICABILITY

According to the present invention, for example, rhDNase I can be provided such a high purity that allows its use as a pharmaceutical medicament.

EXPLANATION OF SIGNS

3a. Internal ribosome binding site originated from mutant type mouse encephalomyocarditis virus including the nucleic acid sequence shown as SEQ ID NO:2
5. Nucleic acid sequence including human EF-1α promoter and first intron
6. SV40 late polyadenylation region
7. Region including SV40 early promoter
8. Synthetic polyadenylation region
10. Glutamine synthetase gene
11. Human DNase I gene

SEQUENCE LISTING FREE TEXT

SEQ ID NO:2=Partial sequence of IRES from mutant type murine encephalomyocarditis virus, synthetic
SEQ ID NO:3=Human DNase I gene-encoding sequence, synthetic
SEQ ID NO:4=Synthetic Construct

What is claimed is:

1. A method of producing purified recombinant human DNase I, comprising:
   (a) culturing recombinant human DNase I-producing mammalian cells in a serum-free medium such that the recombinant human DNase I secretes in the medium;
   (b) collecting culture supernatant by removing the cells from the culture obtained by the culturing;
   (c) subjecting the culture supernatant to anion-exchange column chromatography in the presence of 0.5 to 2.0 mM calcium ions, wherein the recombinant human DNase I binds to the anion exchange resin equilibrated with a butter of pH 7.2 to 7.8 comprising sodium chloride at a concentration of 30 to 70 mM and is eluted from the column using a buffer of pH 4.0 to 5.0 comprising sodium chloride at a concentration of 170 to 230 mill to collect a traction containing the recombinant human DNase I, wherein:
   the anion-exchange column comprises an anion exchange resin comprising a trimethyl ammonium group;
   (d) subjecting the fraction to a column chromatography that employs a solid phase comprising a material having affinity for a phosphate group to collect a fraction containing the recombinant human DNase I;
   (e) subjecting the fraction collected in (d) to cation-exchange column chromatography in the presence of 2 to 20 mM calcium ions, and wherein the recombinant human DNase 1 binds to the cation exchange resin equilibrated with a buffer of pH 4.2 to 4.8 containing sodium chloride at a concentration of 10 to 20 mM and is eluted from the column using a buffer of pH 61 to 7.8 containing sodium chloride at a concentration of 40 to 70 mM to collect a fraction containing the recombinant human DNase I,
   wherein the cation-exchange column comprises a cation exchange resin comprising a sulfa group; and
   (f) subjecting the fraction collected in (e) to a dye affinity column chromatography employing a triazine dye to collect a fraction containing the recombinant human DNase I,
   wherein the purified recombinant human DNase I has a specific activity of 960 U/mg or more.

2. The method according to claim 1, wherein the material having affinity for a phosphate group is fluoroapatite or hydroxyapatite.

3. The method according to claim 2, wherein the material having affinity for a phosphate group is hydroxyapatite.

4. The method according to claim 1, further comprising: subjecting the fraction containing the recombinant human DNase I obtained in (f) to gel filtration column chromatography to collect a fraction containing the recombinant human DNase I.

5. The method according to claim 1, wherein the anion-exchange column chromatography is carried out in the presence of 0.8 to 1.2 mM calcium ions.

6. The method according to claim 1, wherein the cation-exchange column chromatography is carried out in the presence of 0.8 to 1.2 mM calcium ions.

7. The method according to claim 1, wherein the recombinant human DNase I-producing mammalian cells are transformed with an expression vector comprising a human elongation factor-1a promoter, a gene encoding rhDNase I downstream thereof, an internal ribosome entry site derived from 5' untranslated region of murine encephalomyelitis virus further downstream thereof, and a gene encoding a glutamine synthetase still further downstream thereof, and additionally a puromycin or neomycin resistance gene downstream of another gene expression regulatory site.

8. The method according to claim 7, wherein the internal ribosome entry site is derived from 5' untranslated region of wild-type murine encephalomyelitis virus, and a part of two or more start codons in the internal ribosome entry site has been destroyed.

9. The method according to claim 8, wherein the internal ribosome entry site comprises the nucleotide sequence of SEQ ID NO: 2.

10. The method according to claim 1, wherein the recombinant human DNase I-producing mammalian cells are transformed with an expression vector comprising a human elongation factor-1α promoter, a gene encoding rhDNase I downstream thereof, an internal ribosome entry site derived from 5' untranslated region of murine encephalomyelitis virus further downstream thereof, and a gene encoding a glutamine synthetase still further downstream thereof, and additionally a dihydrofolate reductase gene downstream of another gene expression regulatory site.

11. The method according to claim 10, wherein the internal ribosome entry site is derived from 5' untranslated region of wild-type murine encephalomyelitis virus, and a part of two or more start codons in the internal ribosome entry site has been destroyed.

12. The method according to claim 11, wherein the internal ribosome entry site comprises the nucleotide sequence of SEQ ID NO: 2.

* * * * *

SEQUENCE LISTING

<160> NUMBER OF SEQ ID NOS: 4

<210> SEQ ID NO 1
<211> LENGTH: 23
<212> TYPE: DNA
<213> ORGANISM: Murine encephalomyocarditis virus

```
<400> SEQUENCE: 1
atgataatat ggccacaacc atg                                              23

<210> SEQ ID NO 2
<211> LENGTH: 23
<212> TYPE: DNA
<213> ORGANISM: Artificial Sequence
<220> FEATURE:
<223> OTHER INFORMATION: Partial sequence of IRES from mutant type
      murine encephalomyocardinitis virus, synthetic

<400> SEQUENCE: 2
atgataagct tgccacaacc atg                                              23

<210> SEQ ID NO 3
<211> LENGTH: 870
<212> TYPE: DNA
<213> ORGANISM: Artificial Sequence
<220> FEATURE:
<223> OTHER INFORMATION: Human DNaseI gene-encoding sequence, synthetic
<220> FEATURE:
<221> NAME/KEY: CDS
<222> LOCATION: (14)..(862)

<400> SEQUENCE: 3
acgcgtcgcc acc atg agg ggc atg aag ctg ctg ggg gcg ctg ctg gca        49
            Met Arg Gly Met Lys Leu Leu Gly Ala Leu Leu Ala
            1               5                   10 ctg gcg gcc cta ctg cag ggg gcc gtg tcc ctg aag atc gca gcc ttc       97
Leu Ala Ala Leu Leu Gln Gly Ala Val Ser Leu Lys Ile Ala Ala Phe
        15                  20                  25 aac atc cag aca ttt ggg gag acc aag atg tcc aat gcc acc ctc gtc      145
Asn Ile Gln Thr Phe Gly Glu Thr Lys Met Ser Asn Ala Thr Leu Val
    30                  35                  40 agc tac att gtg cag atc ctg agc cgc tat gac atc gcc ctg gtc cag      193
Ser Tyr Ile Val Gln Ile Leu Ser Arg Tyr Asp Ile Ala Leu Val Gln
45                  50                  55                  60 gag gtc aga gac agc cac ctg act gcc gtg ggg aag ctg ctg gac aac      241
Glu Val Arg Asp Ser His Leu Thr Ala Val Gly Lys Leu Leu Asp Asn
                65                  70                  75 ctc aat cag gat gca cca gac acc tat cac tac gtg gtc agt gag cca      289
Leu Asn Gln Asp Ala Pro Asp Thr Tyr His Tyr Val Val Ser Glu Pro
            80                  85                  90 ctg gga cgg aac agc tat aag gag cgc tac ctg ttc gtg tac agg cct      337
Leu Gly Arg Asn Ser Tyr Lys Glu Arg Tyr Leu Phe Val Tyr Arg Pro
        95                  100                 105 gac cag gtg tct gcg gtg gac agc tac tac tac gat gat ggc tgc gag      385
Asp Gln Val Ser Ala Val Asp Ser Tyr Tyr Tyr Asp Asp Gly Cys Glu
    110                 115                 120 ccc tgc ggg aac gac acc ttc aac cga gag cca gcc att gtc agg ttc      433
Pro Cys Gly Asn Asp Thr Phe Asn Arg Glu Pro Ala Ile Val Arg Phe
125                 130                 135                 140 ttc tcc cgg ttc aca gag gtc agg gag ttt gcc att gtt ccc ctg cat      481
Phe Ser Arg Phe Thr Glu Val Arg Glu Phe Ala Ile Val Pro Leu His
                145                 150                 155 gcg gcc ccg ggg gac gca gta gcc gag atc gac gct ctc tat gac gtc      529
Ala Ala Pro Gly Asp Ala Val Ala Glu Ile Asp Ala Leu Tyr Asp Val
            160                 165                 170 tac ctg gat gtc caa gag aaa tgg ggc ttg gag gac gtc atg ttg atg      577
Tyr Leu Asp Val Gln Glu Lys Trp Gly Leu Glu Asp Val Met Leu Met
        175                 180                 185 ggc gac ttc aat gcg ggc tgc agc tat gtg aga ccc tcc cag tgg tca      625
Gly Asp Phe Asn Ala Gly Cys Ser Tyr Val Arg Pro Ser Gln Trp Ser
```

-continued

```
Gly Asp Phe Asn Ala Gly Cys Ser Tyr Val Arg Pro Ser Gln Trp Ser
    190                 195                 200 tcc atc cgc ctg tgg aca agc ccc acc ttc cag tgg ctg atc ccc gac         673
Ser Ile Arg Leu Trp Thr Ser Pro Thr Phe Gln Trp Leu Ile Pro Asp
205                 210                 215                 220 agc gct gac acc aca gct aca ccc acg cac tgt gcc tat gac agg atc         721
Ser Ala Asp Thr Thr Ala Thr Pro Thr His Cys Ala Tyr Asp Arg Ile
                225                 230                 235 gtg gtt gca ggg atg ctg ctc cga ggc gcc gtt gtt ccc gac tcg gct         769
Val Val Ala Gly Met Leu Leu Arg Gly Ala Val Val Pro Asp Ser Ala
            240                 245                 250 ctt ccc ttt aac ttc cag gct gcc tat ggc ctg agt gac caa ctg gcc         817
Leu Pro Phe Asn Phe Gln Ala Ala Tyr Gly Leu Ser Asp Gln Leu Ala
                255                 260                 265 caa gcc atc agt gac cac tat cca gtg gag gtg atg ctg aag tga             862
Gln Ala Ile Ser Asp His Tyr Pro Val Glu Val Met Leu Lys
            270                 275                 280 gcggccgc                                                                870
```

<210> SEQ ID NO 4
<211> LENGTH: 282
<212> TYPE: PRT
<213> ORGANISM: Artificial Sequence
<220> FEATURE:
<223> OTHER INFORMATION: Synthetic Construct

<400> SEQUENCE: 4

```
Met Arg Gly Met Lys Leu Leu Gly Ala Leu Leu Ala Leu Ala Ala Leu
1               5                   10                  15

Leu Gln Gly Ala Val Ser Leu Lys Ile Ala Ala Phe Asn Ile Gln Thr
                20                  25                  30

Phe Gly Glu Thr Lys Met Ser Asn Ala Thr Leu Val Ser Tyr Ile Val
            35                  40                  45

Gln Ile Leu Ser Arg Tyr Asp Ile Ala Leu Val Gln Glu Val Arg Asp
        50                  55                  60

Ser His Leu Thr Ala Val Gly Lys Leu Leu Asp Asn Leu Asn Gln Asp
65                  70                  75                  80

Ala Pro Asp Thr Tyr His Tyr Val Val Ser Glu Pro Leu Gly Arg Asn
                85                  90                  95

Ser Tyr Lys Glu Arg Tyr Leu Phe Val Tyr Arg Pro Asp Gln Val Ser
            100                 105                 110

Ala Val Asp Ser Tyr Tyr Tyr Asp Asp Gly Cys Glu Pro Cys Gly Asn
        115                 120                 125

Asp Thr Phe Asn Arg Glu Pro Ala Ile Val Arg Phe Phe Ser Arg Phe
130                 135                 140

Thr Glu Val Arg Glu Phe Ala Ile Val Pro Leu His Ala Ala Pro Gly
145                 150                 155                 160

Asp Ala Val Ala Glu Ile Asp Ala Leu Tyr Asp Val Tyr Leu Asp Val
                165                 170                 175

Gln Glu Lys Trp Gly Leu Glu Asp Val Met Leu Met Gly Asp Phe Asn
            180                 185                 190

Ala Gly Cys Ser Tyr Val Arg Pro Ser Gln Trp Ser Ser Ile Arg Leu
        195                 200                 205

Trp Thr Ser Pro Thr Phe Gln Trp Leu Ile Pro Asp Ser Ala Asp Thr
210                 215                 220

Thr Ala Thr Pro Thr His Cys Ala Tyr Asp Arg Ile Val Val Ala Gly
225                 230                 235                 240
```

```
Met Leu Leu Arg Gly Ala Val Val Pro Asp Ser Ala Leu Pro Phe Asn
                245                 250                 255

Phe Gln Ala Ala Tyr Gly Leu Ser Asp Gln Leu Ala Gln Ala Ile Ser
                260                 265                 270

Asp His Tyr Pro Val Glu Val Met Leu Lys
            275                 280
```